(12) United States Patent
Chu et al.

(10) Patent No.: US 10,582,938 B2
(45) Date of Patent: Mar. 10, 2020

(54) MEDICAL RETRIEVAL DEVICES AND RELATED METHODS OF USE

(71) Applicant: Boston Scientific Scimed, Inc., Maple Grove, MN (US)

(72) Inventors: Michael S. H. Chu, Brookline, MA (US); Tantra S. Budiman, Newton, MA (US)

(73) Assignee: Bosotn Scientific Scimed, Inc., Maple Grove, MN (US)

( * ) Notice: Subject to any disclaimer, the term of this patent is extended or adjusted under 35 U.S.C. 154(b) by 1469 days.

(21) Appl. No.: 14/475,174

(22) Filed: Sep. 2, 2014

(65) Prior Publication Data

US 2015/0066047 A1    Mar. 5, 2015

Related U.S. Application Data

(60) Provisional application No. 61/872,990, filed on Sep. 3, 2013, provisional application No. 61/903,710, filed on Nov. 13, 2013.

(51) Int. Cl.
| | | |
|---|---|---|
| *A61B 17/221* | (2006.01) | |
| *A61B 17/00* | (2006.01) | |
| *A61B 17/50* | (2006.01) | |

(52) U.S. Cl.
CPC ...... *A61B 17/221* (2013.01); *A61B 17/00234* (2013.01); *A61B 17/50* (2013.01);
(Continued)

(58) Field of Classification Search
CPC ............ A61B 17/221; A61B 17/32056; A61B 17/22031; A61B 2017/2215;
(Continued)

(56) References Cited

U.S. PATENT DOCUMENTS 5,924,175 A * 7/1999 Lippitt ................. A61B 17/221
                                                            24/537
6,152,936 A   11/2000 Christy et al.
(Continued)

FOREIGN PATENT DOCUMENTS

| WO | WO 98/48710 | 11/1998 |
| WO | WO 2010/019776 A2 | 2/2010 |
| WO | WO 2011/057210 A2 | 5/2011 |

OTHER PUBLICATIONS

International Search Report and Written Opinion from corresponding International Application No. PCT/US2014/053726, dated Oct. 10, 2014 (10 pages).

*Primary Examiner* — Ryan J. Severson
*Assistant Examiner* — Socrates L Boutsikaris
(74) *Attorney, Agent, or Firm* — Bookoff McAndrews, PLLC

(57) ABSTRACT

A medical device may include a plurality of branch members having moveable distal portions. The medical device also may include a first moveable member movably connected to the distal portion of one of the branch members at a first location along the branch member. The first moveable member may have first and second proximal portions extending from the first location and disposed within one or more lumens of one or more of the other branch members. The moveable distal portions of the plurality of branch members and the first moveable member may form a first snare movable between a collapsed configuration and an expanded configuration.

19 Claims, 11 Drawing Sheets

(52) U.S. Cl.
CPC .............. *A61B 2017/00358* (2013.01); *A61B 2017/2215* (2013.01)

(58) Field of Classification Search
CPC .. A61B 2017/2212; A61B 2017/00358; A61B 2017/22034; A61B 2017/22035; A61B 17/50; A61F 2002/011
USPC ....................................... 606/127, 113, 200
See application file for complete search history.

(56) References Cited

U.S. PATENT DOCUMENTS

| | | |
|---|---|---|
| 6,383,195 B1 | 5/2002 | Richard |
| 2003/0225419 A1 | 12/2003 | Lippitt et al. |
| 2007/0027456 A1 | 2/2007 | Gartner et al. |
| 2011/0112548 A1* | 5/2011 | Fifer .............. A61B 17/320016 606/129 |

* cited by examiner

MEDICAL RETRIEVAL DEVICES AND RELATED METHODS OF USE

CROSS-REFERENCE TO RELATED APPLICATIONS

This application claims the benefit of priority from U.S. Provisional Application No. 61/872,990, filed on Sep. 3, 2013, and U.S. Provisional Application No. 61/903,710, filed Nov. 13, 2013, the entireties of which are incorporated by reference herein.

TECHNICAL FIELD

The present disclosure relates generally to medical retrieval devices and related systems and methods. More specifically, the present disclosure relates to devices, systems, and methods for retrieving objects within a patient.

BACKGROUND

Medical retrieval devices are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, and gallbladder. Minimally invasive medical procedures are used to remove these concretions through natural orifices, or through an incision, such as during a percutaneous nephrolithotomy (PNCL) procedure. Further, lithotripsy and ureteroscopy, for example, are used to treat urinary calculi (e.g., kidney stones) in the ureter of a patient.

Further, known medical retrieval devices are complex, requiring many components and labor-intensive manufacturing processes. The assembly of small parts often requires visual magnification and specialized training. The available joining mechanisms often increase the profile of the medical retrieval devices beyond optimal design parameters, and are often the weakest structural points. These drawbacks result in medical retrieval devices that are bulky, expensive, and prone to failure.

Thus, there remains a need for improved medical retrieval devices having reduced profiles and fewer components.

SUMMARY OF THE DISCLOSURE

The present disclosure includes medical retrieval devices and related methods of use.

In accordance with an embodiment, the present disclosure is directed to a medical device which may have a plurality of branch members having moveable distal portions; a first moveable member movably connected to the distal portion of one of the branch members at a first location along the branch member, the first moveable member having first and second proximal portions extending from the first location and disposed within one or more lumens of one or more of the other branch members, wherein the moveable distal portions of the plurality of branch members and the first moveable member form a first snare movable between a collapsed configuration and an expanded configuration.

Aspects of the medical device may include one or more of the following: a middle portion of the first moveable member may be movably connected to the distal portion of one of the plurality of branch members; the first and second proximal portions of the first moveable member may enter the lumen via a distal end opening of the another one of the plurality of branch members, the first and second proximal portions of the first moveable member may enter the lumen via a distal end side wall opening of the another one of the plurality of branch members, distal portions of the plurality of branch members may have a preset shape to the expanded configuration, proximal ends of the first moveable member may exit the lumen of the another one of the plurality of branch members and connect to an actuating member, the actuating member may be configured to provide a tensioning force on the proximal ends of the first moveable member to collapse the first snare and move toward the collapsed configuration, proximal portions of the plurality of branch members may be parallel and extend from a sheath member, each of the plurality of branch members may comprise a side wall aperture, each of the side wall apertures may be disposed on a distal end of each of the plurality of branch members, a portion of the first moveable member may be movably connected to the distal portion of one of the plurality of branch members at the side wall aperture and each end of the first moveable member may enter the lumen of the another one of the plurality of branch members via a different one of the side wall apertures of the another one of the plurality of branch members, each of the branch members may comprise a side wall aperture and a second moveable member movably connected to the distal portion of one of the branch members at a first location and having first and second proximal portions disposed in a lumen of one of the branch members, wherein the moveable distal portions of the plurality of branch members and the second moveable member may form a second snare movable between a collapsed configuration and an expanded configuration, wherein a portion of the second moveable member may be movably connected to the distal portion of one of the plurality of branch members at a side wall aperture, wherein the first and second proximal portions of the second moveable member enter the lumen of one of the branch members via an aperture, the first and second proximal portions of the second moveable member may each enter the lumen of one of the branch members via a different end of the aperture, the second snare may be proximal to the first snare, proximal ends of the second moveable member may exit the lumen of the another one of the plurality of branch members and connect to an actuating member configured to provide a tensioning force on the proximal ends of the second moveable member to collapse the second snare and may move radially biased distal portions of the branch members closer together, the branch members may include one or more stationary members coupled to a tubular member at least one of the stationary members may have a distal portion comprising a loop knot attached to the first moveable member.

In accordance with an embodiment, the present disclosure is directed to a medical device which may include a first branch member having a moveable distal portion; a second branch member having a moveable distal portion; a first moveable member movably connected to the distal portion of the first branch member at a first location along the first branch member, the first moveable member having first and second proximal portions disposed within a lumen of the second branch member, wherein the moveable distal portions of the first and second branch members and the first moveable member form a first snare movable between a collapsed configuration and an expanded configuration; and a second moveable member movably connected to the distal portion of the first branch member at a second location and having first and second proximal portions disposed in the lumen of the second branch member, wherein the moveable distal portions of the first and second branch members and the second moveable member form a second snare movable between a collapsed configuration and an expanded configuration.

In accordance with an embodiment, the present disclosure is directed to a medical device which may include a first branch member having a moveable distal portion; a second branch member having a moveable distal portion; a first moveable member movably connected to the distal portion of the first branch member at a first location along the first branch member, the first moveable member having first and second proximal portions disposed within a lumen of the second branch member, wherein the moveable distal portions of the first and second branch members and the first moveable member form a first snare movable between a collapsed configuration and an expanded configuration; a second moveable member movably connected to the distal portion of the first branch member at a second location and having first and second proximal portions disposed in the lumen of the second branch member, wherein the moveable distal portions of the first and second branch members and the second moveable member form a second snare movable between a collapsed configuration and an expanded configuration; and an actuating member connected to proximal ends of the first and second moveable members.

In accordance with an embodiment, the present disclosure is directed to a medical device which may have a basket moveable between a collapsed configuration and an expanded configuration. The basket may include three or more branch members each having a lumen, and a plurality of moveable members. The moveable members may each have a first portion connected to a distal end of one of the branch members and a second and third portion connected at a location proximal of the distal end of another one of the branch members. The medical device may include an actuating member configured to move the basket member between the collapsed configuration and the expanded configuration.

In accordance with an embodiment, the present disclosure is directed to a medical device which may have a basket moveable between a collapsed configuration and an expanded configuration. The basket may include three or more branch members each having a lumen, and a plurality of moveable members. The moveable members may each have a first portion connected to a distal end of one of the branch members and a second and third portion connected at a location proximal of the distal end of another one of the branch members, and portions of the moveable members may cross each other. The medical device may include an actuating member configured to move the basket member between the collapsed configuration and the expanded configuration.

In accordance with an embodiment, the present disclosure is directed to a medical device having a basket moveable between a collapsed configuration and an expanded configuration. The basket may consist essentially of a plurality of branch members each having a lumen, an equal number of moveable members as the branch members, each moveable member coupled to one branch member with end portions extending into apertures of adjacent branch members, and an actuating member configured to move the basket member between the collapsed configuration and the expanded configuration

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
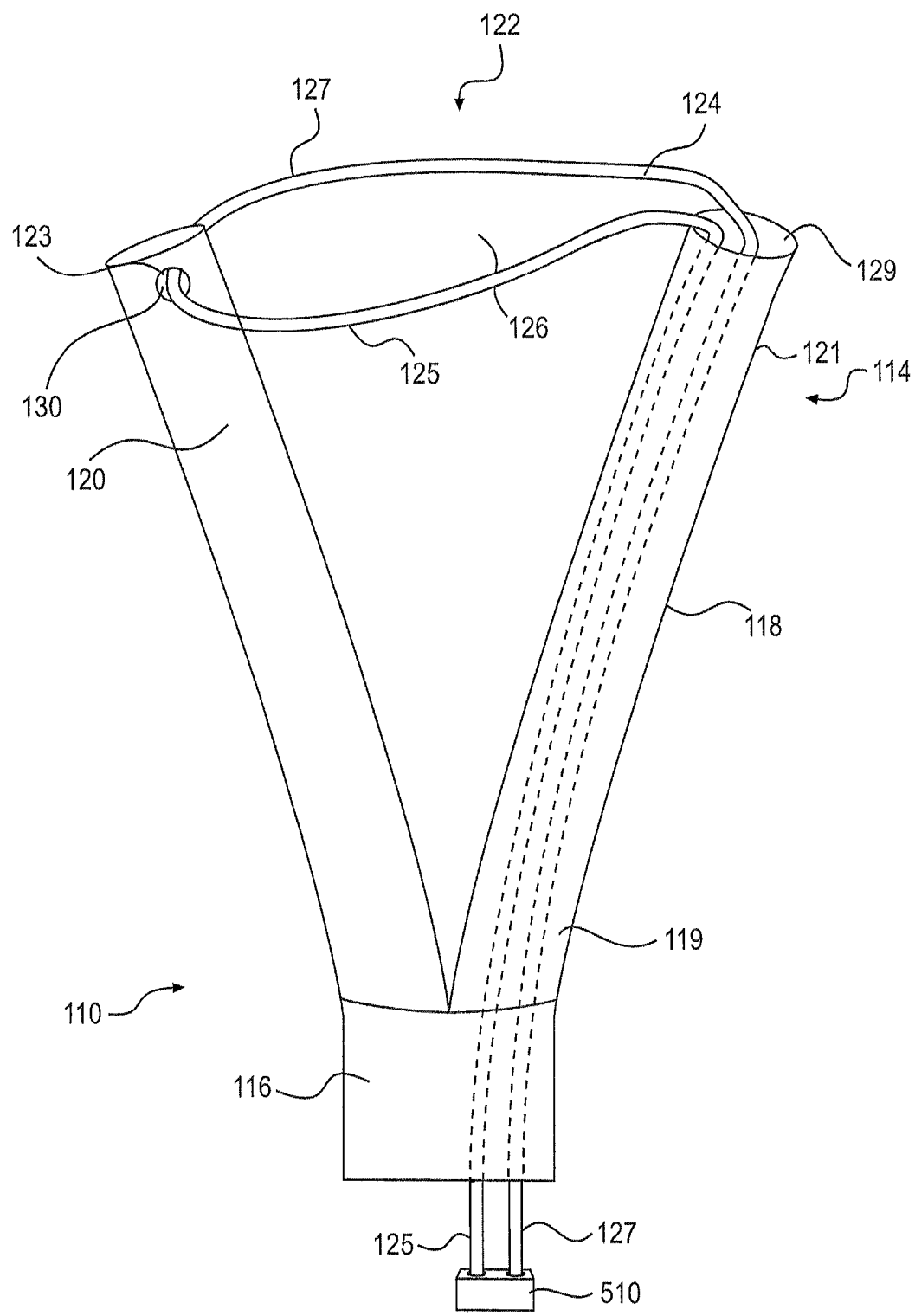
FIG. 1 is a partial side view illustration of a portion of a medical retrieval device in an expanded configuration in accordance with an embodiment of the present disclosure.
Figure 2:
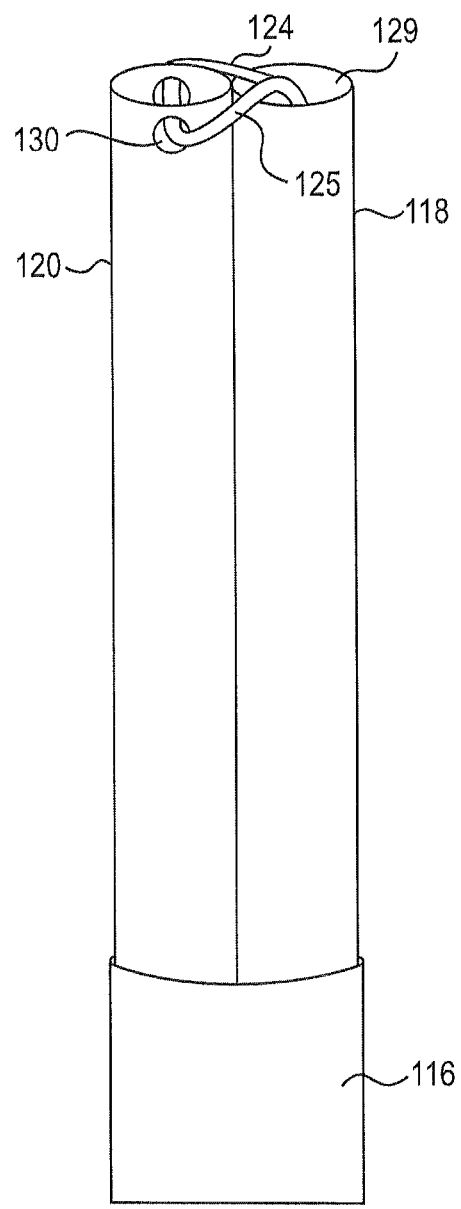
FIG. 2 is a partial side view illustration of a portion the medical retrieval device of FIG. 1 in a closed configuration.
Figure 5:
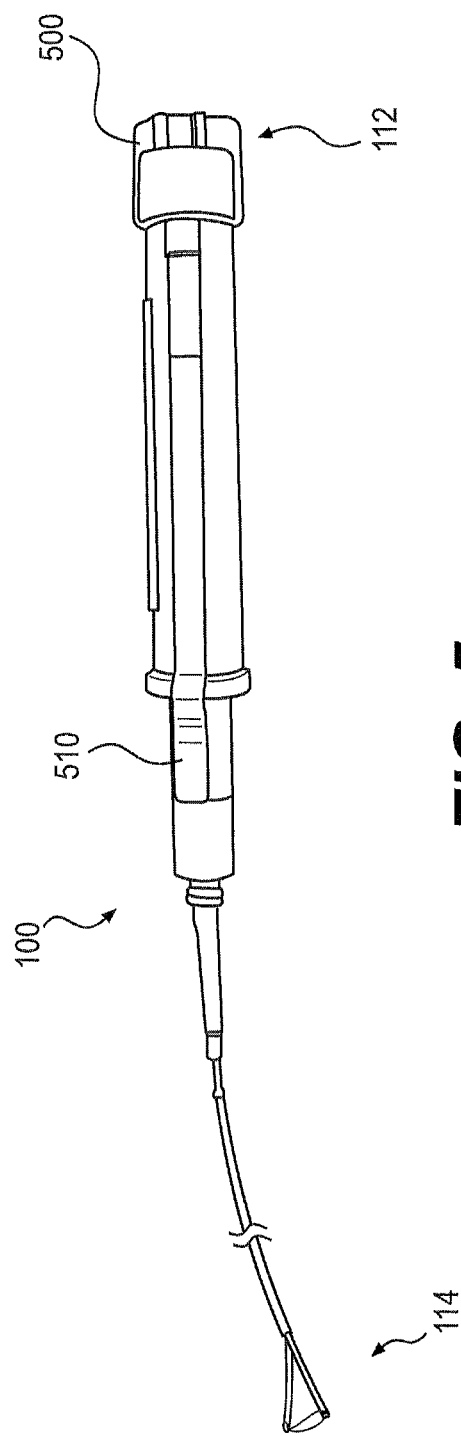
FIG. 5 is a side view illustration of a handle assembly for use with a medical retrieval device in accordance with the present disclosure.

As shown in FIGS. 1 and 5 a medical device 100 according to an exemplary embodiment of the present disclosure may extend from a proximal end 112 toward a distal end 114. An enlarged view of the distal end 114 of the medical device 100 is shown in FIG. 1. In this view, the distal end 114 is in an expanded configuration. FIG. 2 shows the medical device 200 in a collapsed configuration. The medical device 100 may be used to retrieve matter in the body, such as stones from the ureter, kidney, bladder (KUB) through a natural orifice or through an incision such as in a percutaneous nephrolithotomy (PCNL) procedure, gripping and/or ligating matter in the body.

The medical device 100 may also be used in a different portion of the human anatomy and may be configured to fit through a working channel of another medical device, such as a ureteroscope, or other medical device, having a diameter suitable for entry into the body, such as about 1 to about 4 French in diameter, e.g. about 3 French in diameter and may be configured to retrieve matter of any suitable size, such as about 1 mm to 12 mm in diameter.

Medical device 100 may include two or more branch members 118 and 120. Each branch member 118 and 120 may have a stationary proximal portion 119 and a moveable distal portion 121, which may move between radially open positions (FIG. 1) to a substantially linear position (FIG. 2). The proximal portions 119 of the branch members 118, 120 may be adjacent one another and may be disposed within and extend from a sheath member 116.

In some embodiments, the branch members 118 and 120, may be substantially similar, and be formed in a tubular shape having a lumen. The branch members 118 and 120 may be formed of a polymer or a metal such as PET, peek, polyimide, nitinol, stainless steel or the like and have thin wall about 0.001" thick and have an inner diameter of about 0.009". The tube profile may be any suitable shape, size, or geometry, such as round, square, rectangular, oval, or polygonal in cross sectional profile. One or more branch member 118 and/or 120 may have any suitable geometric profile so that they may have a very low profile when in a collapsed configuration. For example, each branch member 118 and 120 may have flat complimentary shaped surfaces, which may fit into each other when the branch members are collapsed. In another example, if the device includes three or more branch members, each branch member may have a triangular shape having flat profiles. The branch members 118 and 120 may be connected at the proximal portions 119 by sheath 116 using any suitable means or combination of means, such as heat shrinking, gluing, and heat bonding or in any other preferred manner. Alternatively, the branch members 118 and 120 may not be substantially similar wherein, for example, one branch member could be a solid member while the other branch member could be hollow.

The medical device 100 also may include one or more moveable members 124. Portions of the moveable member 124 may be positioned at the distal end 114 of the device 100 and attached to the distal portion 121 of one of the branch members 118 or 120 in any suitable manner. For example, the moveable member 124 may form a snare 122 by securing a portion, such as a midpoint, of the moveable member 124 to a distal portion 121 of branch member 120 at an attachment location 123. Attachment location 123 may be disposed on an outer surface of branch member 120 and the moveable member 124 may be secured to the attachment location by glue or any other fixing arrangement. As shown in FIG. 1, the fixing may be via an aperture 130 (e.g. hole, slot) extending through the branch member 120. In this example, the moveable member 124 may be movably connected to the branch member 120 at the aperture 130. The aperture 130 may be formed in any suitable manner, such as by laser cutting, mechanical cutting, punching, etc. One or more portions of the branch members 118 and/or 120, for example in areas surrounding the aperture 130, may be reinforced in any suitable manner.

The moveable member 124 may be a single strand or filament wire, a monofilament or braided wire, sutures, rope, or the like. The moveable member 124 may be manufactured using any suitable material or combination of materials and may be flexible and have sufficient stiffness and strength to move the branch members 118 and 120 from a radially expanded position to a substantially linear position, either by transferring a tensioning force or a pushing force from the actuating member 510, associated with handle 500, (shown in FIG. 5). The moveable member 124 may be a metal, a polymer, or a combination of materials such as a metal wire that is coated with a plastic (polymer) jacket, or for example, two metals co-drawn together. The moveable member 124 may have various properties including elasticity and flexibility, for reaching around various body matter and entrapping matter. In addition, one or more portions of the movable member 124 may include one or more friction coatings and/or coatings having various properties such as therapeutic, radiopacity, etc. The moveable member 124 may be continuous from one end to the other end. In another example, the moveable member 124 may be manufactured by connecting multiple sections of same or different materials, profiles, properties, etc. The moveable member 124 may have a round, square, rectangular, oval, or polygonal in cross sectional profile. For example, the moveable member 124 may be a filament, a certain portion of which may be flattened, machined, removed, extruded, drawn, bent, notched, roughened, heat set, or etched to a different or preferred profile. In one example, the moveable member 124 may be a nitinol wire with an outside diameter of about 0.004".

Two ends of the moveable member 124 extending from the fixed portion of the moveable member 124 secured to the branch member 120 may enter a lumen of branch member 118 via a distal opening in branch member 118, such as a sidewall aperture, distal end opening 129 as shown in FIG. 1, or any other suitable opening. After entering distal end opening 129, two ends 125 and 127 may extend proximally through the lumen of branch member 118 and connect to the actuating member 510 associated with a handle at 500 (FIG. 5) so that the ends move together with the actuating member 510. In another example, the moveable member 124 may form a loop and cross itself to form an intersection. A loose knot may be formed at the intersection. Furthermore, the branch members 118 and 120 may be solid and the moveable member 124 may be movably attached to each branch member via a coupling, such as a groove, protrusion, etc., formed along the branch member. In this manner, the branch members may have a lower profile than branch members having a lumen.

The actuating member 510 may exert a tensioning force on the proximal portions of the moveable member 124 to move the snare 122 to a collapsed configuration as shown in FIG. 2, with the distal portions 121 of the branch members 118 and 120 moved from radially biased positions to an adjacent orientation. For example, branch members 118 and 120 may be pre-formed with a radial bend towards an expanded configuration (FIG. 1) and the actuating member 510 may exert a tensioning force on proximal portions of the moveable member 124, having sufficient strength to move the branch members 118 and 120 to a substantially linear orientation. Conversely, releasing the tensioning of the moveable member 124 or moving the actuating member 510 in a distal direction may allow the branch members 118 and 120 to return or recover to their pre-formed expanded configuration to expand the snare 122.

In another example, distal portions 121 of the branch members 118 and 120 may be pre-formed as substantially linear, and the actuating member 510 may exert a pushing force on the moveable members 124, the moveable member 124 having a sufficient stiffness to move the branch members 118 and 120 to the expanded configuration and thereby expanding the snare 122. Conversely, releasing the pushing force of the moveable member 124 and/or moving the actuating member 510 proximally may allow the branch member 118 and 120 to return or recover to its substantially linear configuration (FIG. 2) and collapse the snare 122.

In the expanded configuration as shown in FIG. 1, the snare 122 may easily be positioned around a body object, in space 126, such as a ureteral stone, and the snare 122 may be transitioned to a collapsed configuration (FIG. 2) to ligate and/or capture objects for removal or repositioning.

Figure 3:
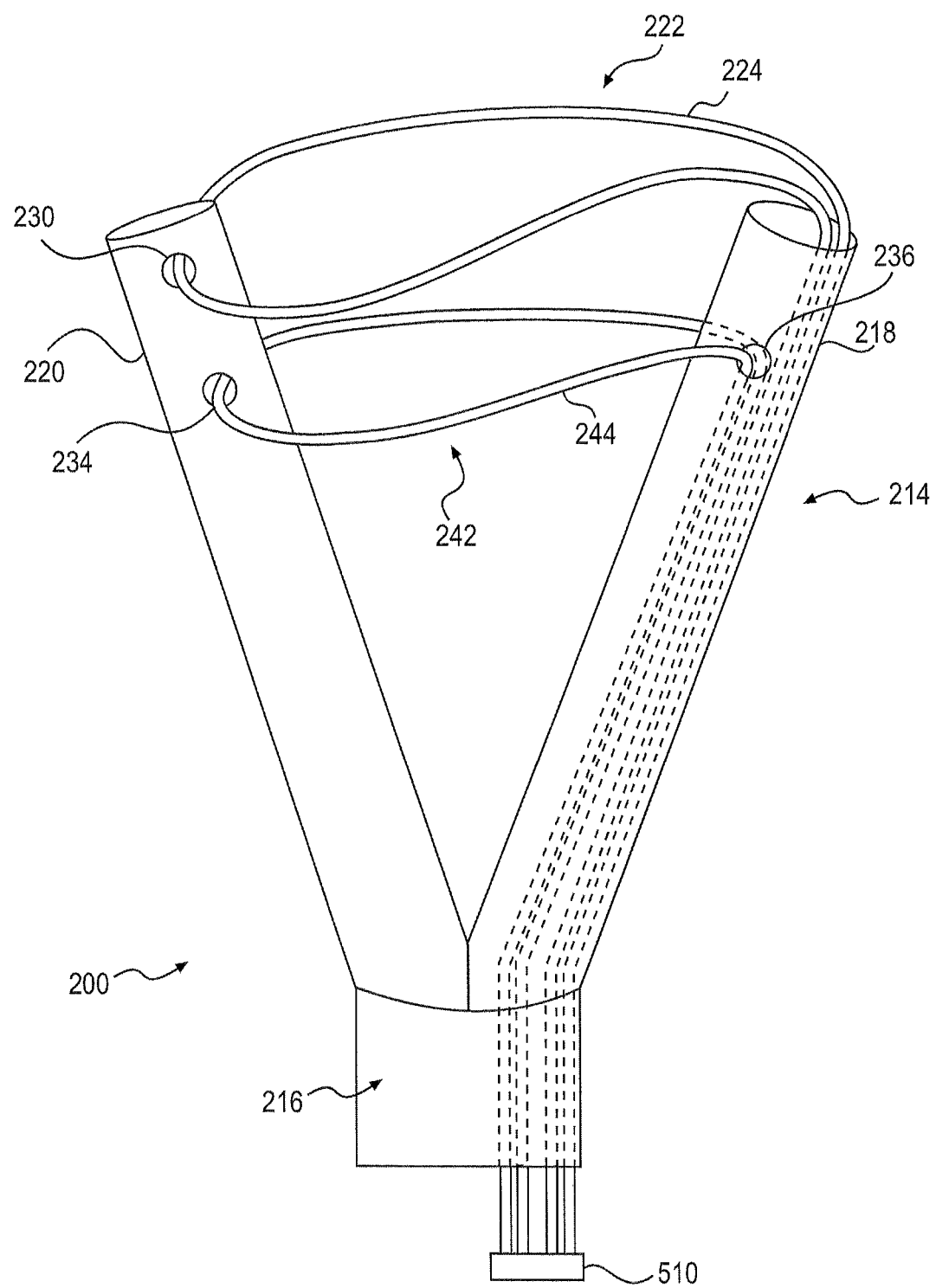
FIG. 3 is a partial side view illustration of a portion a medical retrieval device in an expanded configuration in accordance with another embodiment of the present disclosure.

In another embodiment shown in FIG. 3, the medical device 100 may include a distal end 214 similar to the distal end 114 shown in FIGS. 1 and 2, except that the distal end 214 includes a second snare or second loop 242 in addition to a snare 222. The first and second snare 222, 242 may expand and collapse simultaneously via the activation of the actuating member 510 associated with handle, 500 (FIG. 5). The second snare 242 may be parallel or positioned on a second layer or tier proximal the first snare 222. The second snare 242 may aid in capturing smaller targets, providing a greater capture area (e.g. depth), where smaller targets may be ligated and/or captured by the branch members 218 and 220. The greater capture depth may allow greater amplitude in visually gauging the smaller target in reference to the capturing snares 222 and 242. The first snare 222 may be assembled similarly to the snare 122 as described above in the distal end 114 of FIG. 1.

The second snare 242 may include two additional apertures 234 and 236 through both branch members 218 and 220 proximal the first snare 222. The second snare 242 may be formed of a second moveable member 244.

Portions of the second moveable member 244 may be attached to an aperture 234 or 236 of one of the branch members 118 or 120 in any suitable manner such as a knot, glue, etc. For example, the second moveable member 244 may form the snare 242 by securing a portion of the second moveable member 244 to a distal portion of branch member 220 at an aperture 234. Two ends of the moveable member 244 may then extend from the portion secured to branch member 220 at apertures 234, to an aperture 236 on the other branch member 218. Each end of second moveable member 244 may enter the lumen of branch member 218 via aperture 236 on branch member 218. Similar to branch member 120, the branch member 220 may be a hollow tube, partially hollow, a solid member.

After entering apertures 236, the two ends of moveable member 244 may extend proximally through the lumen of branch member 218 and may then connect to an actuating member 510 associated with a handle 500 (FIG. 5). In this manner, all four moveable member ends of the moveable members 224, 244 may be connected to the actuating member 510, such that each end may be displaced an equal distance by the activation of the actuation member 510 to open and close each snare 222 and 242 simultaneously. Similar to the distal end 114 (FIG. 1) of medical device 100, the moveable member 222 may extend through a distal end of branch member 218 or extend through apertures or openings formed in the distal end of branch member 218, similar to apertures 236. Further, moveable members 224 and/or 244 may be reversed to be fixed to branch member 218 and extend proximally through branch member 220 to actuator 510.

Figure 4:
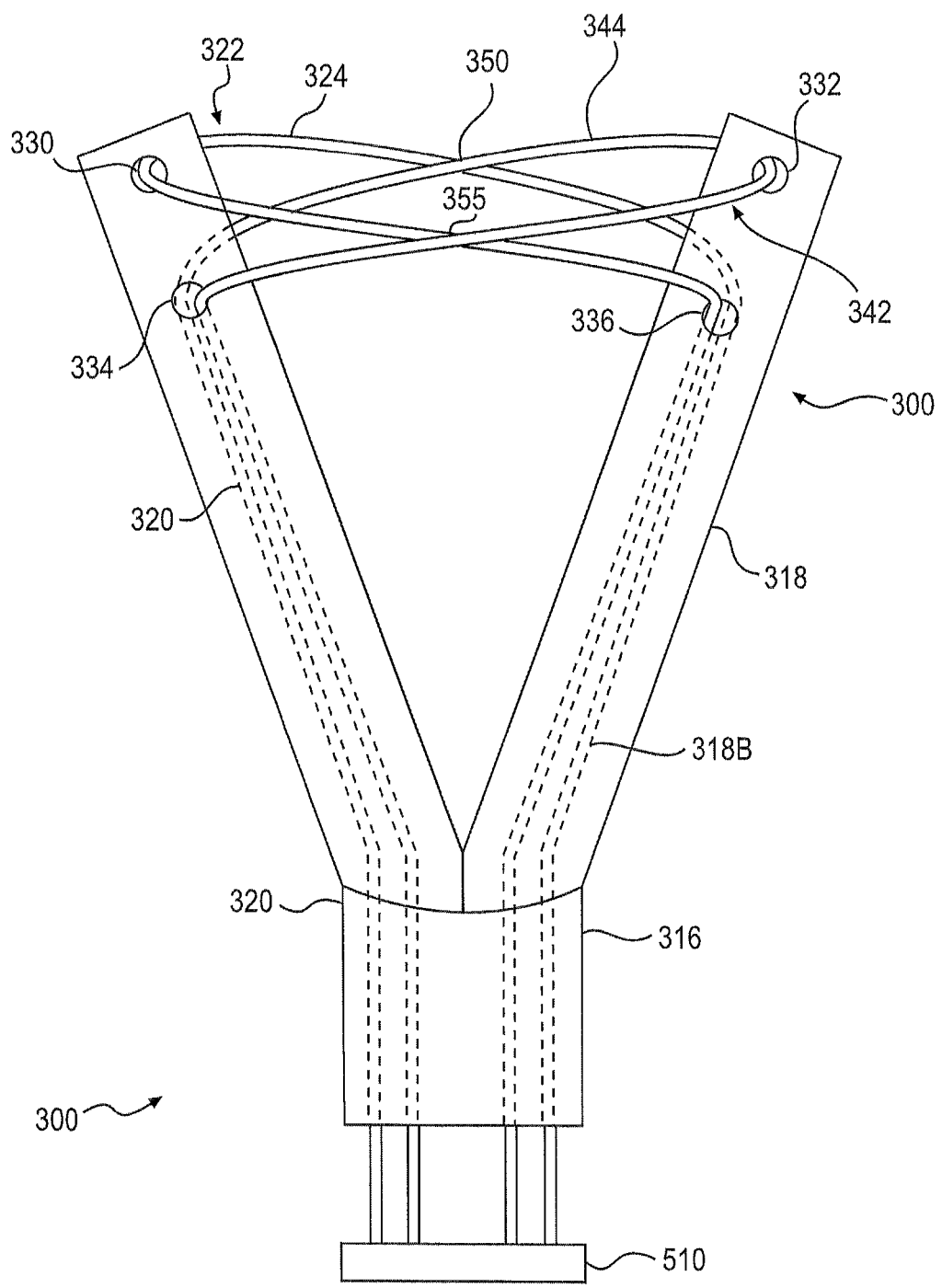
FIG. 4 is a partial side view illustration of a portion a medical retrieval device in an expanded configuration in accordance with another embodiment of the present disclosure.

FIG. 4 shows a similar distal end 314 of medical device 100 as that of distal end 114 described above with reference to FIGS. 1 and 3, except the moveable members of the snares may be oriented in a manner such that portions of snares 322 and 342 may cross or intersect, for example, at 350 and 355. This orientation in which portions of the snares 322 and 342 may cross or intersect may enable the snares 322 and 342 to capture small targets. Each branch 318 and 320 of medical device 300 may include apertures along the length of the branch members, for example, branch member 318 may have a distal aperture 332 and a proximal aperture 336, and branch member 320 may have a distal aperture 330 and an aperture 334. As shown in FIG. 4, a first moveable member 324 forming a first snare 322 may be inserted through distal aperture 330 of branch member 320 and secured thereto. Each ends of moveable member 324 may be inserted into proximal aperture 336 of branch member 318 and into the lumen of branch member 318. A second moveable member 344 forming second snare 342 may be inserted through proximal aperture 334 of branch member 320 and secured thereto. The ends of moveable member 344 may be inserted into distal aperture 332 of branch member 318 and into the branch member lumen. The moveable members 344 and 324 may cross or intersect at locations 350 and 355. Multiple moveable members may cross over or intersect to form multiple cross over points configured to capture body matter, such as concretions. It is understood that in this embodiment and the other embodiments of this disclosure, the securing of the moveable members to a branch member may be achieved by feeding the moveable members through the aperture, without other fixing or securing. Thus, the moveable member may slide within the apertures.

In an alternative arrangement, the moveable members disclosed above may be replaced with moveable members that may be bent to form a portion coaxial with the branch member and a portion substantially perpendicular to the branch member. For example, the moveable members may each be bent at about 90 degrees to form perpendicular collapsible portions and coaxial stationary portions. The stationary portions maybe secured to an open end of a branch member via glue, adhesive or any other suitable manner. The moveable member may enter the lumen of another branch member lumen via apertures of another branch member, and may attach to an actuator 510, in the same manner disclosed above.

As shown in FIGS. 6-8 and 14, a medical device 600 according to an exemplary embodiment of the present disclosure may extend from a proximal end 612 closest to the user, to a distal end 614, closest to a patient target site. The medical device 600 may include an expandable snare and/or basket 616 disposed at the distal end 614.

Figure 7:
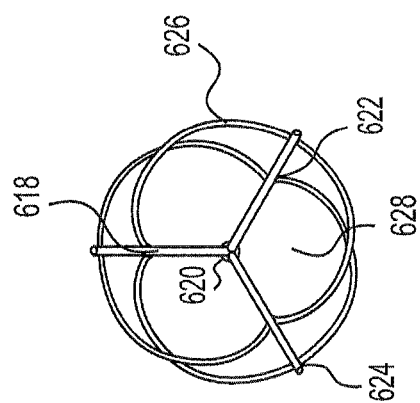
FIGS. 6 and 7 are partial side view and top view illustrations, respectively, of a distal portion of a medical retrieval device in an expanded configuration in accordance with an embodiment of the present disclosure.
Figure 6:
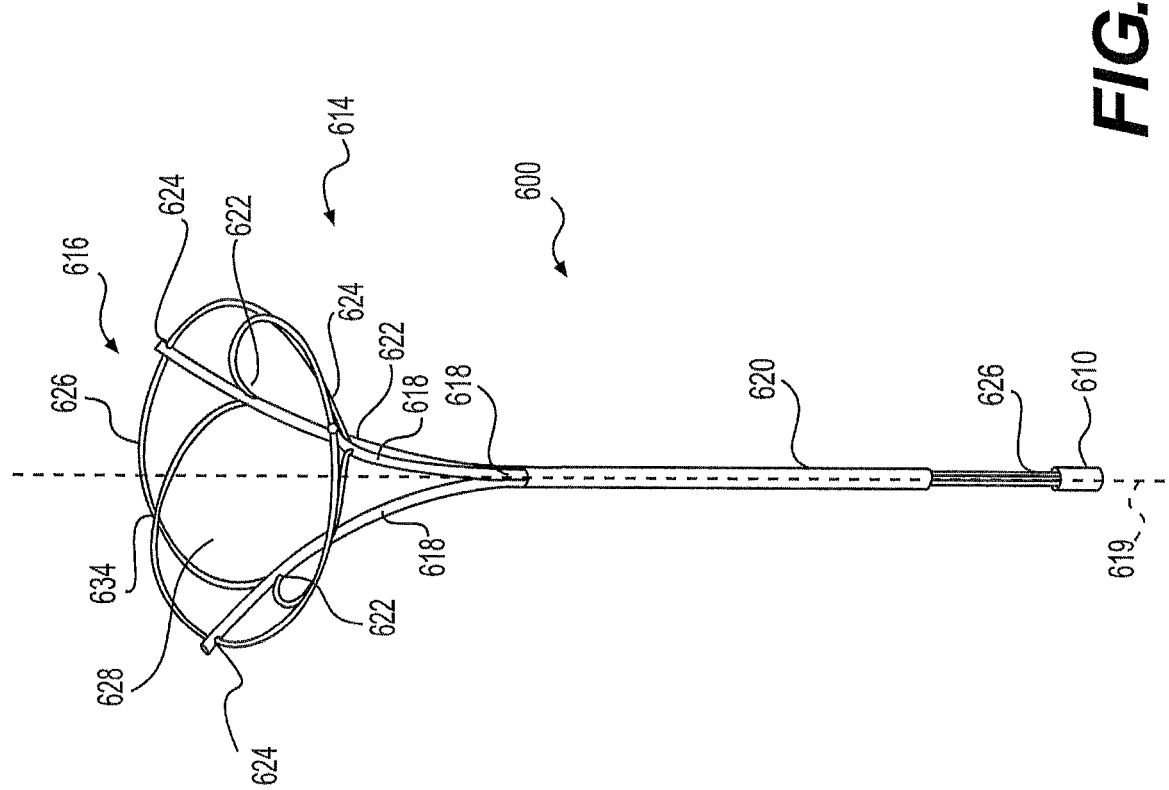
Figure 8:
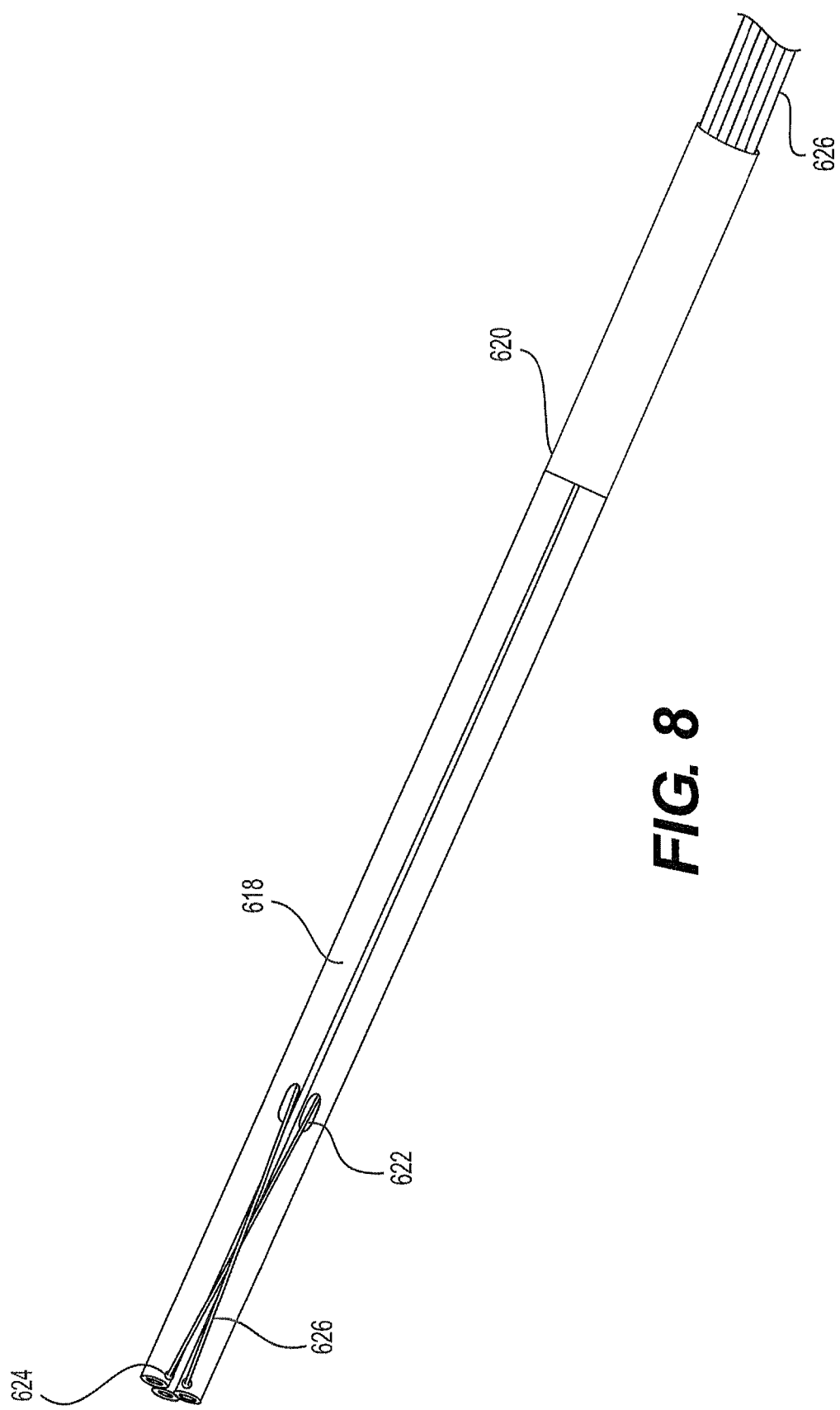
FIG. 8 is a partial side view illustration of a portion of the medical retrieval device of FIGS. 6 and 7 in a collapsed configuration.

The basket 616 may include a plurality of elongate branch members 618 and a plurality of moveable members 626. FIGS. 6 and 7 illustrate the basket 616 in an expanded configuration. In the expanded configuration, distal portions of elongate branch members 618 may be disposed radially outward from a longitudinal axis 619, and connected to portions of moveable members 626 forming a basket 616. The distal portions of the branch members 618 may be spaced apart from one another in a uniform or non-uniform distribution and may be moveable from radially extended positions to substantially linear positions (FIG. 8). For example, in the embodiment shown in FIGS. 6 and 7, medical device 600 may include three branch members 618, the distal ends of which may be extended away from the longitudinal axis 619 and spaced about 120° from one another. However, it should be noted that any other suitable number of branch members 618 might alternatively be utilized.

The branch members 618 may be naturally biased, formed, or pre-bent, or pre-disposed in any suitable manner to extend radially from the longitudinal axis 619 in a neutral, non-forced configuration. Alternatively, branch members 618 may be formed to have a substantially linear neutral position and may be forced to extend radially from the longitudinal axis 619.

Proximal portions of branch members 618 may be parallel, stationary, and adjacent and may be disposed within one or more sheath members 620, such as a heat shrink member. Proximal portions of branch members 618 disposed within sheath member 620 may be connected together adjacent a distal end of the sheath member 620 and may terminate adjacent the distal end of sheath member 620.

In some embodiments, the branch member 618, may be formed in a tubular shape having a lumen. Branch member 618 may be formed using any suitable materials. In one embodiment, branch member 618 may be manufactured using two or more co-axial polymer tubes, such as, e.g., polyimide, and polyethylene terephthalate (PET), among others. The use of more than one tube for a branch member 618 may strengthen areas where apertures are present in the branch member 618. The additional tube(s) may extend the entire length of branch member 618, or along only a portion of the branch member 618. The tube may be made using the same or different materials. For example, additional tube portions may be positioned adjacent and surrounding the branch member 618 and apertures may be made using a material having a greater strength than other portions of the branch member 618. Alternatively, branch member 618 may be manufactured using a single polymer tube. Branch member 618 may have any suitable circumferential wall thickness and internal diameter. In one example, a branch member may have a wall thickness of about 0.001 inches, and an internal diameter (ID) of about 0.005 inches, though any other suitable wall thickness and internal diameter suitable for use in the body may alternatively be utilized.

Branch members 618 may include attachment portions configured to attach or secure a portion of moveable member 626 forming basket 616. In the embodiment of FIGS. 6-8 and 14, branch member 618 may include one or more distal apertures 624 and one or more proximal apertures 622. Each distal aperture 624 also may be circumferentially and longitudinally aligned with another distal aperture 624. Similarly, proximal apertures 622 may be circumferentially and longitudinally aligned. The distal apertures 624 also may be circumferentially aligned with the proximal apertures 622. It is understood, however, that such circumferential and longitudinal alignments may be omitted. The apertures 622, 624 may have any suitable size, shape, or geometry and may be formed by any suitable method, such as laser cutting or mechanical cutting. For example, branch member 618 may include a generally circular proximal apertures 622 and distal apertures 624 formed through branch member 618. In some embodiments, the apertures 622 and 624 may have a slot shape configured to assist movement of the moveable member 626 within the branch member 618. The location of the apertures 622 and 624 may vary depending on the desired configuration of the basket 616 and its use. The proximal apertures 622 and distal apertures 624 may be spaced apart from each other by any suitable distance, for example 0.10 inches to 0.30 inches. Alternatively, distal aperture 624 could be replaced with open distal tips of the branch member 618. Further, the apertures 622 and 624 could be other than circular, such as oval-shaped as shown in FIG. 8 with respect to the proximal apertures 622. Branch members 618 may extend the same distance away from the distal end of sheath 620 or may have varying lengths. Branch members 618 may curve in the same arc profile and same planar orientation away from longitudinal axis 619 or may have different profiles or different orientations with respect to longitudinal axis 619. The distal ends of member 618 may be angled in any of three dimensions away from distal end of sheath 620.

Movable members 626 may be formed using any suitable material. Materials may include, but are not limited to, metals, polymers, or a combination of materials, having suitable flexibility, strength, and/or stiffness to move the branch members 618 between expanded and collapsed conditions. In one embodiment, one or more moveable members 626 may be formed using a metal wire, such as nitinol. Portions or the entire length of the moveable members 626 may be coated with a polymer. In an alternative embodiment, the moveable members 626 may be formed from two or more metals that are co-drawn together. The moveable member 626 may have any suitable size and cross-sectional profile such as, e.g., circular, rectangular, oval shaped, or polygonal. In some embodiments, portions of the moveable members 626 may be flattened, machined, extruded, drawn, or etched into a different profile than a remaining portion of moveable members 626. The cross-sectional profiles of members 626 may vary at any point along their length, for example by tapering or flattening. Each moveable member 626 may be formed of the same material(s) or different material(s). In some embodiments, the moveable members 626 may be slotted to allow deflection or directional bending. In one embodiment, the moveable members 626 may be formed with a super elastic, elastic or shape memory material, such as, e.g., Nitinol wires having any suitable diameter. All or portions of the exterior surfaces of the branch members 618 and/or the moveable member 626 may be roughened, notched, slotted, etched, sand-blasted, or otherwise modified to provide a better gripping surface.

The moveable members 626 may be inserted through one or more apertures of the branch member 618, such as the proximal and distal apertures 622 and 624. For example, a moveable member 626 may be inserted through a distal aperture 624 of one branch members 618 so that portions of the moveable member 626 extend from both sides of the aperture 624. For example, moveable member 626 may extend through aperture 624 so that the aperture 624 is located at a midpoint of the moveable member 626. Moveable member 626 may be rigidly fixed to aperture 624 in any suitable manner, such as adhesive, glue, solder, welding, crimping, etc., or may be slidable within aperture 624. Alternatively, moveable member 626 may be rigidly fixed to a distal end of a branch member 618 without the use of a distal aperture 624.

As shown in FIGS. 6 and 7, each end of the moveable member 626 extending from the distal aperture 624 may be inserted into a proximal aperture 622 of a different circumferentially adjacent branch member 618. The moveable member 626 may then enter a lumen of the branch member 618 through apertures 622, and exit from a proximal end of a lumen of the branch member 618 and connect to an actuating member 610. The actuating member 610 may be associated with a handle 1420 (FIG. 14) and may be configured to interface with a user's hand. The actuating member 610 may have any suitable configuration, such as a sliding button, knob, lever, dial, finger pull, etc. The actuating member 610 may be configured to exert or release a tensioning force, or exert or release a pushing force on the moveable member 626 to transition the branch member 618 between the open and closed configurations shown in FIGS. 6 and 8 respectively. The proximal end of the moveable member 626 may be operatively coupled to the actuating member 610 either via direct attachment, for example via a crimp, adhesive, weld, etc. In another embodiment, the proximal end of the moveable member 626 may be coupled to a drive wire (not shown) which in turn may be couple to the actuating member 610 in any suitable manner.

In one embodiment, a distal portion of branch member 618 may be moved to the parallel linear position of FIG. 8 by the actuating member 610 exerting a tensioning or pulling force on moveable member 626, thereby collapsing basket 616, and tensioning branch member 618 so as to orient the distal the portion of branch member 618 in a linear parallel position (FIG. 8). In another example, branch member 618 may be moved, and basket 616 expanded, by the actuating member 610 exerting a pushing force on moveable member 626, which in turn forces the branch member 618 radially outwardly at its distal end. In the examples described above, the branch member 618 may have sufficient flexibility and other properties to move orientations and positions, and the moveable member 626 may have sufficient flexibility and/or stiffness and other suitable properties to transfer forces from the actuating member 610 to the branch member 618 to move the branch member 618. As shown in FIG. 6, the basket 616 may be generally round; however, the branch member 618 and moveable member 626 may be arranged in any size, shape, and configuration to provide a desired basket profile upon deployment that may not be generally round e.g. elliptical, clover shaped, etc.

Three branch members 618 and three moveable members 626 are shown in the embodiment of FIGS. 6-8 and 14. Thus, three moveable members 626 may each be positioned so that an end of the moveable member 626 extending from a distal aperture 624 may be inserted or threaded into proximal aperture 622 of a different circumferentially adjacent branch member 618. In this manner, a moveable member 626 may enter the lumens of different branch members 618 via apertures 622 and may be connected (six in total) to common actuating member 610, associated with handle 1420. The snare or basket 616 may include a distal first tier where the moveable member 626 is inserted into the distal aperture 624 of branch member 618, and a proximal second tier where the moveable member 626 enters the proximal aperture 622. The distal and proximal tiers may be spaced apart from each other by any suitable distance, which may correspond to the distance between the distal and proximal apertures 624, 622 of the branch member 618. The basket 616 formed by the moveable members 626 coupled to each branch member 618, may form a front opening 628, and the moveable members 626 forming the basket 616 may cross each other at one or more locations 634.

As noted above, in some embodiments, distal portions of the branch member 618 may be naturally biased (e.g., pre-bent, predisposed, or curved) such that in the expanded configuration of FIGS. 6 and 7, the branch member 618 may extend radially outward from longitudinal axis 619 when forces are not applied to the branch member 618. In other embodiments, distal portions of the branch member 618 may be substantially linear and parallel in their un-forced state, and the moveable member 626 may be of a sufficient stiffness to assist in rapidly extending the branch member 618 away from the longitudinal axis 619. In some embodiments, some moveable members 626 may be fixed in place while one or more other moveable members 626 may move relative to the branch member 618 or to other moveable members 626. In some embodiments, the distal end of the basket 616 may be flared like a trumpeter bell, cylindrical, curled inward like a tulip, or shaped in any other suitable manner useful to the deployment, performance, and removal of the basket 616 with the body of the patient. Moveable member 626 may bend in and direction around the distal end to create the desired basket opening profile and to enhance performance of the device.

The branch members 618 may be positioned such that the front opening 628 may be oriented around a target site in the body, such as a kidney stone. The branch members 618 may be retracted from the open or expanded configuration shown in FIGS. 6 and 7 by moving the proximal ends of the moveable members 626 proximally, which may in turn decrease the distance between branch members 618.

Figure 10:
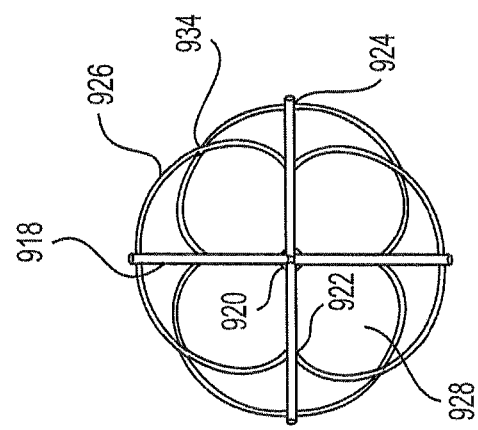
FIGS. 9 and 10 are partial perspective and top view illustrations respectively of a distal portion a medical retrieval device in an expanded configuration in accordance with another embodiment of the present disclosure.
Figure 9:
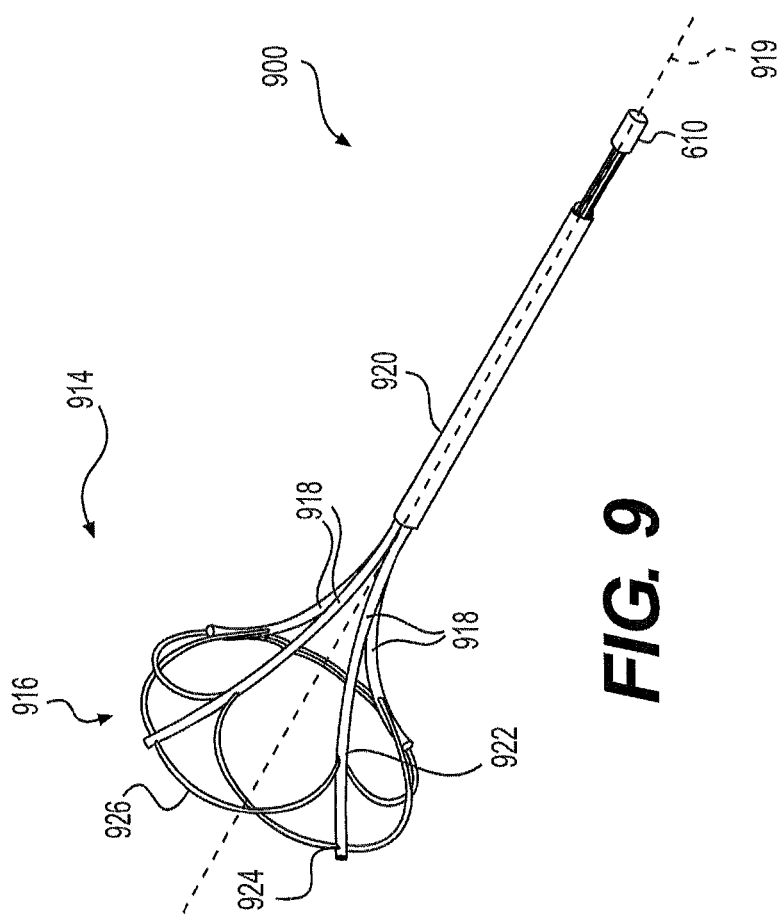

FIGS. 9 and 10 show a medical device 900 according to another exemplary embodiment of the present disclosure similar to medical device 600 in FIGS. 6-8, except, medical device 900 includes four branch members 918, and four moveable members 926. Thus, the features discussed above with respect to FIGS. 6-8 may be included in the embodiment of FIGS. 9 and 10. For example, distal end 900 of medical device 600 may include an expandable snare or basket 916 forming a front opening 928 disposed at the distal end 914, and elongate branch members 918, the distal ends of which may be radially moveable from a longitudinal axis and spaced about 90° from one another. Proximal portions of branch members 918 may be parallel, stationary, and adjacent and may be disposed within one or more sheath members 920, such as a heat shrink member. Branch members 918 also may include proximal apertures 922 and/or distal apertures 924 in the same manner as described above with respect to apertures 622 and 624 of FIGS. 6-8.

Figure 11:
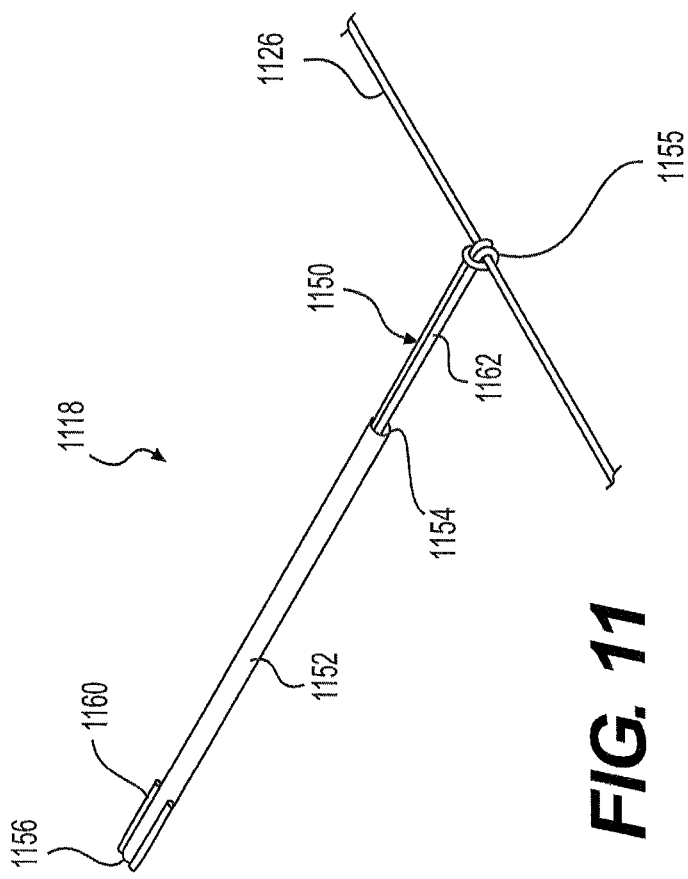
FIG. 11 is a partial perspective view illustration of a distal portion of a component of a medical retrieval device in accordance with another embodiment of the present disclosure.

As shown in FIG. 11, the branch members 618, 918 of the previous embodiments may be replaced by branch members 1118. Thus, the features discussed above with respect to FIGS. 6-10 and 14 may be included in the embodiment of FIG. 11. Branch members 1118 may include one or more stationary members 1150 disposed through a lumen of a tube member 1152 and may extend distally out of a distal aperture 1154 and proximally from a proximal end opening 1156. The distal aperture 1154 may by formed as a distal end opening of the tube member 1152. The proximal end of the stationary member 1150 may be secured to the tube member 1152 via any suitable manner, e.g. by folding over as shown in FIG. 11, and/or by further securing mechanisms such as adhesive, solder, etc. The distal end 1162 of the stationary member 1150 may extend a distance distal of the distal aperture 1154 of the branch member 1118. The distance that the distal end 1162 of the stationary member 1150 may extend from the distal aperture 1154 of the tube member 1152 may be any suitable distance and may correspond to the distance between the distal and proximal apertures 624 and 622 of branch member 618 shown in FIG. 6.

The distal end 1162 of the stationary member 1150 may form a loop and secure a portion of a moveable member 1126, at a location, such as the midpoint of the moveable member 1126. Alternatively, moveable member 1126 may be coupled to stationary member 1150 via a knot, weld, crimp, heat shrink, polymer tube (e.g. polyimide), glue, or any other suitable means. Each end of the moveable member 1126 may enter the lumen of a different circumferentially adjacent branch member 1118 via a distal aperture 1154 of a tube member 1152 of another branch member 1118, such as a circumferentially adjacent branch member 1118 and exit proximally from the lumen of another branch member 1118 in a similar manner as discussed regarding moveable members 626 and 926 in FIGS. 6-10 and 14.

Figure 12:
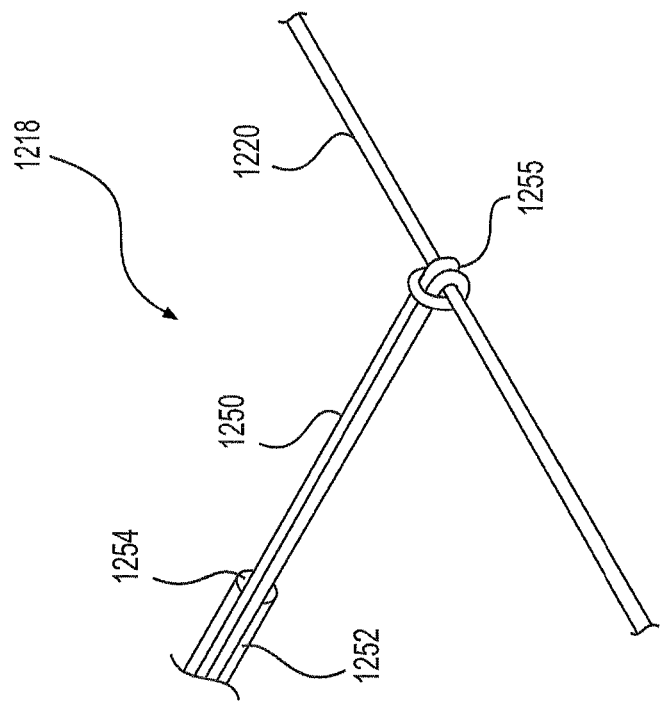
FIG. 12 is a partial perspective view illustration of a distal portion of a component of a medical retrieval device in accordance with another embodiment of the present disclosure.

As shown in FIG. 12, the branch members 618, 918, and 1118 of the previous embodiments may be replaced by branch member 1218. Thus, the features discussed above with respect to FIGS. 6-11 and 14 may be included in the embodiment of FIG. 12. Branch member 1218 may be similar in most aspects to the device shown in FIG. 11 except the stationary member 1250 of the branch member 1218 may be disposed on an outer surface of a tubular member 1252. The stationary member 1250 may extend a distance distal of the elongate member 1252 and secure a moveable 1220, for example, via a loop knot 1255. Each end of the moveable member 1220 may enter the lumen of a different circumferentially adjacent branch member 1218 via a distal aperture 1254 of the branch member 1218 and exit proximally from the lumen of the tube member 1252 of another branch member 1218 in a similar manner as discussed regarding moveable members 626 and 926 in FIGS. 6-10 and 14.

Figure 13:
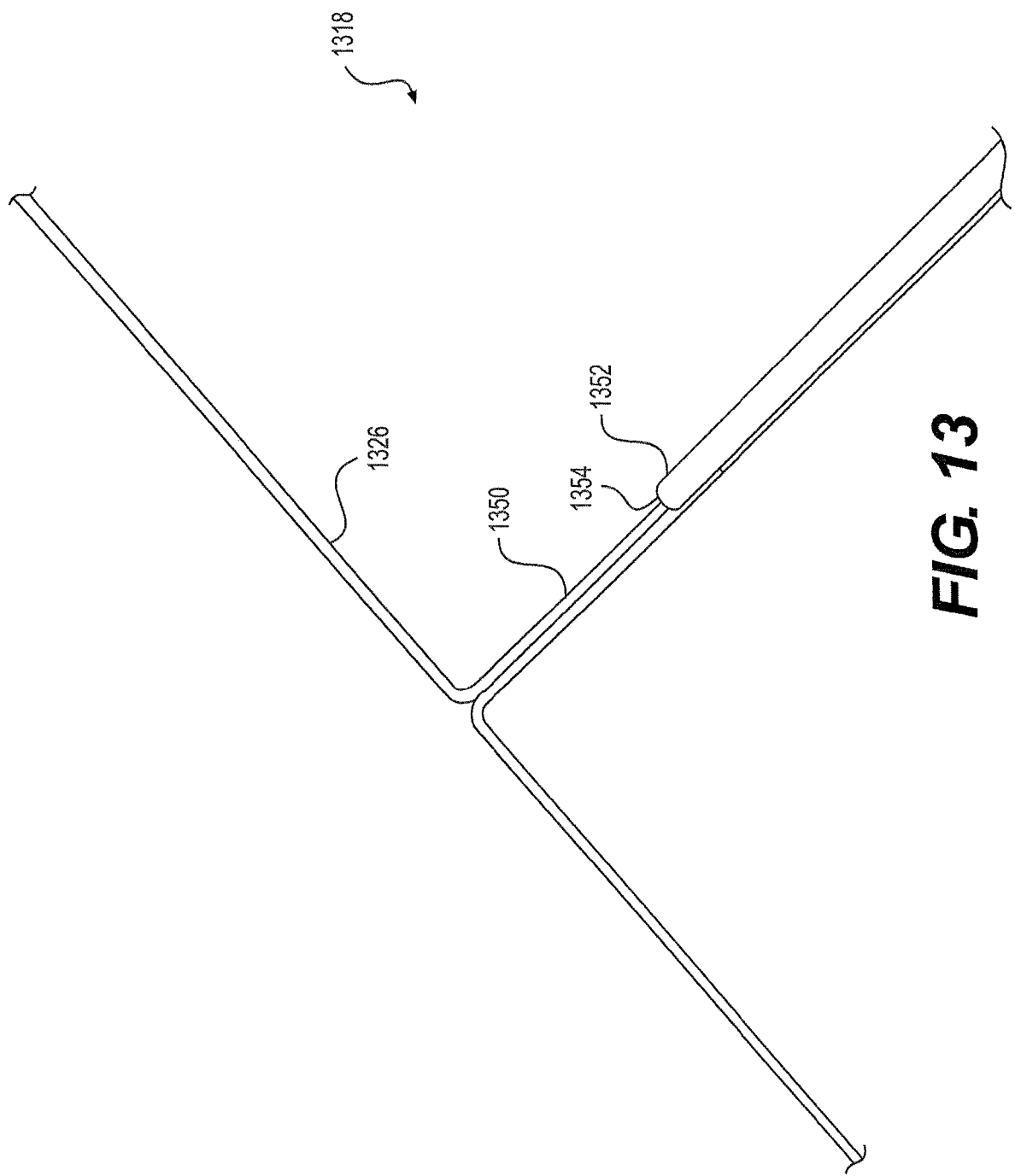
FIG. 13 is a partial perspective view illustration of a distal portion of a component of a medical retrieval device in accordance with another embodiment of the present disclosure.
Figure 14:
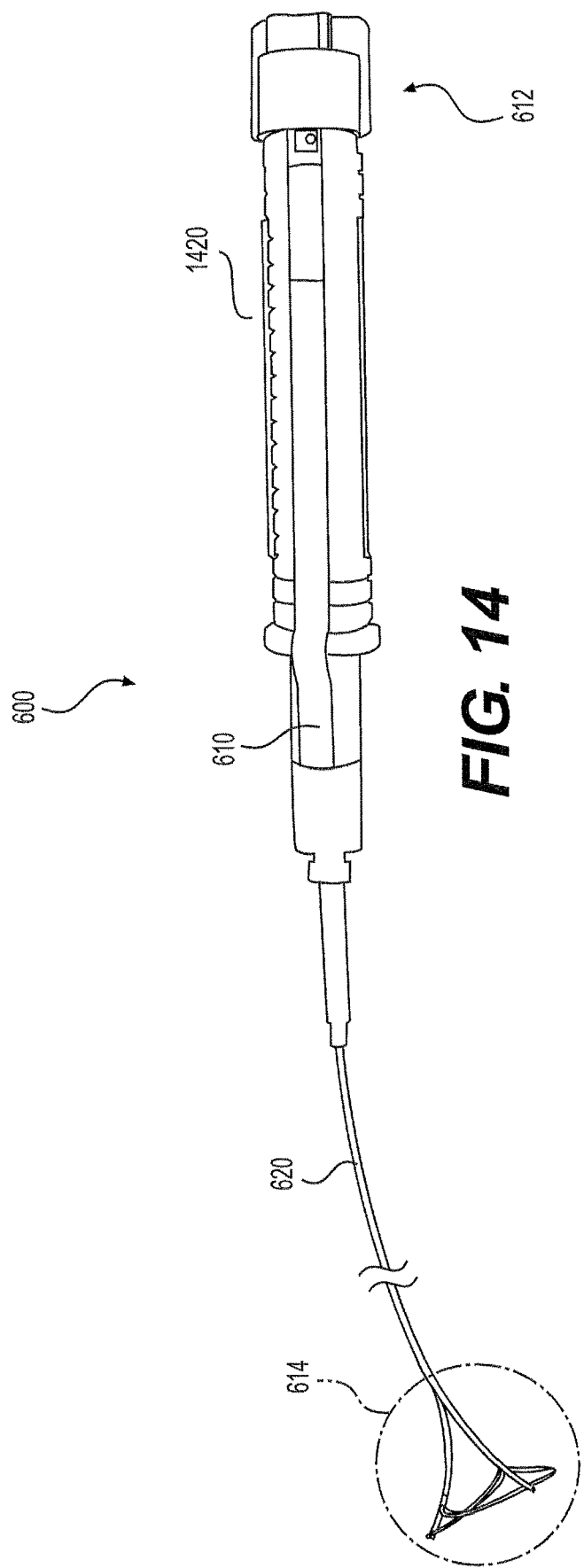
FIG. 14 is a side view illustration of a medical retrieval device in accordance with an embodiment of the present disclosure.

As shown in FIG. 13, the branch members 618, 918, 1118, and 1218 of the previous embodiments may be replaced by branch member 1318. Thus, the features discussed above with respect to FIGS. 6-12 and 14 may be included in the embodiment of FIG. 13. Branch member 1318 may be similar in most aspects to the device shown in FIG. 12 except the moveable member 1326 may be formed from a distal end of stationary member 1350. The stationary member 1350 may extend a distance distal of the tubular member 1352. For example, each branch member 1318 may include two elongate members, each of which may be bent or otherwise formed into a moveable member 1326 and a stationary member 1350. The two stationary members 1350 of each branch member 1318 may be secured to each other by any suitable manner, such as via a clip or with an adhesive. The stationary member 1350 may be attached to tubular member 1352. For example, the stationary member 1350 may be extend along and be secured to an outside surface of the tubular member 1352, or be disposed within a lumen of the tubular member 1352. Each end of the moveable member 1326 may enter the lumen of a different circumferentially adjacent branch member 1318 proximally via a distal opening 1354 of the branch member 1318 and exit from the lumen of the branch member 1318 proximally in a similar manner as discussed regarding moveable members 626 and 926 in FIGS. 6-10 and 14.

In the expanded configuration, a user may manipulate medical devices disclosed herein to capture materials within a patient, such as, e.g., a kidney stone or the like. Materials may enter the basket, for example, basket 616 via a front or side opening defined by adjacent branch members 618.

Any aspect set forth in any embodiment may be used with any other embodiment set forth herein. Every device and apparatus set forth herein may be used in any suitable medical procedure, may be advanced through any suitable body lumen and body cavity, and may be used to remove material from any suitable body portion. For example, the apparatuses and methods described herein may be used through any natural body lumen or tract, including those accessed orally, vaginally, rectally, nasally, urethrally, or through incisions in any suitable tissue. The device described in this disclosure achieves a small profile having with few moving parts and joints.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

We claim:

1. A medical device, comprising:
a plurality of branch members having moveable distal portions, wherein each of the plurality of branch members includes a first side wall aperture and a second side wall aperture, wherein the second side wall aperture is positioned distally of the first side wall aperture, each of the first side wall aperture and the second side wall aperture being positioned along the moveable distal portion and proximally of a distalmost end of the branch member, each of the first side wall aperture and the second side wall aperture having an axis extending through a side wall of the movable distal portion, wherein the axis of the side wall aperture is angled relative to the side wall, wherein the first side wall aperture of each of the branch members is circumferentially aligned, and wherein the second side wall aperture of each of the branch members is circumferentially aligned;
a plurality of moveable members, wherein a first moveable member of the plurality of moveable members is movably connected to the distal portion of one of the branch members at a first location along the one of the branch members, the first moveable member having first and second portions extending from the first location, at least one of the first and second portions extending through the first side wall aperture of the one of the branch members and being disposed within a lumen of another branch member of the plurality of branch members, wherein the moveable distal portions of the plurality of branch members and the first moveable member form a snare or basket movable between a collapsed configuration and an expanded configuration.

2. The medical device of claim 1, wherein a middle portion of the first moveable member is movably connected to the distal portion of the one of the plurality of branch members.

3. The medical device of claim 1, wherein the distal portions of the plurality of branch members have a preset shape to the expanded configuration.

4. The medical device of claim 1, wherein both proximal ends of the first moveable member connect to an actuating member for movement therewith.

5. The medical device of claim 4, wherein the actuating member is configured to provide a tensioning force on the proximal ends of the first moveable member to collapse the snare or basket and move toward the collapsed configuration.

6. The medical device of claim 1, wherein proximal portions of the plurality of branch members are parallel and extend from a sheath member.

7. The medical device of claim 1, wherein the plurality of branch members includes at least three branch members.

8. The medical device of claim 7, wherein the at least one of the plurality of branch members is a first branch member and wherein the another of the plurality of branch members is a second branch member, and a further branch member of the at least three branch members is a third branch member, wherein the first portion of the first moveable member being disposed within the lumen of the second branch member and the second portion being disposed within a lumen of the third branch member.

9. The medical device of claim 1, wherein the plurality of branch members includes at least four branch members.

10. The medical device of claim 1, wherein each of the plurality of branch members further includes a distal end opening positioned distally of the second side wall aperture.

11. A medical device, comprising:
a first branch member having a moveable distal portion;
a second branch member having a moveable distal portion;
a first moveable member directly and movably connected to the distal portion of the first branch member at a first location along the first branch member via a first side wall aperture of the first branch member, wherein the first side wall aperture is proximal of a distalmost end of the first branch member; and
a second moveable member directly and movably connected to the distal portion of the first branch member at a second location along the first branch member via a second side wall aperture of the first branch member, wherein the second location is proximal of the first location;
wherein each of the first moveable member and the second moveable member is moveably connected to the distal portion of the second branch member.

12. The medical device of claim 11, further including a third moveable member.

13. The medical device of claim 12, further including a third branch member having a moveable distal portion.

14. The medical device of claim 12, wherein the first moveable member includes first and second portions, the first portion being disposed within a lumen of the second branch member and the second portion being disposed within a lumen of the third branch member.

15. The medical device of claim 11, wherein the second branch member includes a first side wall aperture and a second side wall aperture, wherein the first side wall aperture of each of the first and second branch members is circumferentially aligned, and wherein the second side wall aperture of each of the first and second branch members is circumferentially aligned.

16. A medical device, comprising:
a first branch member having a moveable distal portion;
a second branch member having a moveable distal portion;
a first moveable member movably connected to and contacting the distal portion of the first branch member at a first location along the first branch member, the first moveable member having first and second portions;
a second moveable member movably connected to and contacting the distal portion of the first branch member at a second location and having first and second portions, wherein the second location is distal to a proximal end of the first branch member, and wherein each of the first and second locations are proximal of a distalmost end of the first branch; and
an actuating member connected to proximal ends of the first and second moveable members.

17. The medical device of claim 16, further including a third moveable member and a third branch member having a moveable distal portion, wherein the third moveable member includes a proximal end coupled to the actuating member.

18. The medical device of claim 17, further including a fourth moveable member and a fourth branch member having a moveable distal portion, wherein the fourth moveable member includes a proximal end coupled to the actuating member.

19. The medical device of claim 16, wherein the second branch member includes a first side wall aperture and a second side wall aperture, wherein the first side wall aperture of each of the first and second branch members is circumferentially aligned, and wherein the second side wall aperture of each of the first and second branch members is circumferentially aligned.

* * * * *